United States Patent [19]

Dunseath, Jr.

[11] Patent Number: 4,669,479
[45] Date of Patent: Jun. 2, 1987

[54] DRY ELECTRODE SYSTEM FOR DETECTION OF BIOPOTENTIALS

[75] Inventor: W. J. Ross Dunseath, Jr., Durham, N.C.

[73] Assignee: Spring Creek Institute, Inc., Durham, N.C.

[21] Appl. No.: 767,963

[22] Filed: Aug. 21, 1985

[51] Int. Cl.⁴ ............................................. A61B 5/04
[52] U.S. Cl. ................................ 128/640; 128/644; 128/696; 128/902
[58] Field of Search ............................ 128/639–641, 128/643, 644, 696, 902, 798, 802, 803

[56] References Cited

U.S. PATENT DOCUMENTS

| | | | |
|---|---|---|---|
| 3,029,808 | 4/1962 | Kagan | 128/639 |
| 3,372,107 | 3/1968 | Klein | 252/512 |
| 3,500,823 | 3/1970 | Richardson et al. | 128/639 |
| 3,542,013 | 11/1970 | Stephenson | 128/696 |
| 3,565,059 | 2/1971 | Hauser et al. | 128/640 |
| 3,565,060 | 2/1971 | Sipple | 128/696 |
| 3,566,860 | 3/1971 | Moe | 128/641 |
| 3,572,322 | 3/1971 | Wade | 128/640 |
| 3,572,323 | 3/1971 | Yuan | 128/640 |
| 3,605,728 | 9/1971 | Ogle | 128/696 |
| 3,606,881 | 9/1971 | Woodson | 128/641 |
| 3,620,208 | 11/1971 | Higley et al. | 128/639 |
| 3,628,527 | 12/1971 | West | 128/639 |
| 3,679,989 | 7/1972 | Thibodeau | 330/185 |
| 3,743,538 | 7/1973 | Mungaard | 427/88 |
| 3,744,482 | 7/1973 | Kaufman et al. | 128/639 |
| 3,750,094 | 7/1973 | Zenkich | 128/641 |
| 3,752,151 | 8/1973 | Robichaud | 128/641 |
| 3,805,769 | 4/1974 | Sessions | 128/641 |
| 3,828,766 | 8/1974 | Krasnow | 128/641 |
| 3,882,846 | 5/1975 | Fletcher et al. | 128/640 |
| 3,911,906 | 10/1975 | Reinhold, Jr. | 128/640 |

(List continued on next page.)

FOREIGN PATENT DOCUMENTS

| | | | |
|---|---|---|---|
| 00000759 | 2/1979 | European Pat. Off. | 128/640 |
| 2,735,050 | 2/1979 | Fed. Rep. of Germany | 128/640 |
| 2,045,088 | 10/1980 | United Kingdom . | |

OTHER PUBLICATIONS

Rositano et al., "Ultra-Soft Dry Electrodes . . . ", Med. Inst., vol. 7, #1, Jan.-Feb. 1973, p. 76.
Betts et al., "Method . . . Unprepared Skin", Med. & Biol. Eng., vol. 14, No. 3, pp. 313-315, May 1976.
ISAM: Proceedings of the Third International Symposium on Ambulatory Monitoring, 1979, "Some Developments in Ambulatory Monitoring of the EGG", R. J. Quy et al. The National Hospital for Nervous Disease, London, UK, pp. 393-398.
Med. & Biol. Eng. & Comput, 1980, 18, pp. 199-122, Technical Note "Hybrid Amplifier-Electrode Module for Measuring Surface Electromyographic Potentials, Van der Locht, Van der Straaten, Vredenbregt.
Biomedical Electrode Technology, "Dry Electrodes and Electrode Amplifiers; W. H. Ko et al. pp. 168-181.

Primary Examiner—Lee S. Cohen
Attorney, Agent, or Firm—Oblon, Fisher, Spivak, McClelland & Maier

[57] ABSTRACT

A dry electrode system for the detection of biopotentials existing on the surface of the skin of a living body, including a dry electrode pad with a resilient conductive pad adhering to at least one adhesive pad or otherwise having opposed adhesive surfaces, one of which is adapted to engage the skin of said living body. The dry electrode pad makes electrical connection to an amplifying circuit which transmits a biopotential derived from the conductive pad to a monitor. The amplifying circuit includes a conductive input contact for making electrical contact to the conductive pad, a lead amplifier having an input coupled to the input contact, and a voltage driven shield coupled to the output of the lead amplifier and surrounding portions of the input contact not in engagement with the dry electrode pad.

61 Claims, 13 Drawing Figures

U.S. PATENT DOCUMENTS

| | | | |
|---|---|---|---|
| 3,928,244 | 12/1975 | Passmore | 252/520 |
| 3,943,918 | 3/1976 | Lewis | 128/640 |
| 3,976,055 | 8/1976 | Monter et al. | 128/641 |
| 3,998,215 | 12/1976 | Anderson et al. | 128/640 |
| 4,026,278 | 5/1977 | Ricketts et al. | 128/644 |
| 4,051,842 | 10/1977 | Hazel et al. | 128/640 |
| 4,077,397 | 3/1978 | Ellis et al. | 128/641 |
| 4,077,398 | 3/1978 | Ellis | 128/641 |
| 4,088,133 | 5/1978 | Twentier | 128/644 X |
| 4,121,573 | 10/1978 | Crovella et al. | 128/640 |
| 4,122,843 | 10/1978 | Zdrojkowaki | 128/644 |
| 4,125,110 | 11/1978 | Hymes | 128/640 |
| 4,141,366 | 2/1979 | Cross, Jr. et al. | 128/798 |
| 4,191,195 | 3/1980 | Miller | 128/696 |
| 4,200,109 | 4/1980 | McMorrow, Jr. | 128/696 |
| 4,202,344 | 5/1980 | Mills et al. | 128/644 |
| 4,209,020 | 6/1980 | Nielsen | 128/640 |
| 4,217,908 | 8/1980 | Staver | 128/643 |
| 4,235,241 | 11/1980 | Tabuchi et al. | 128/639 |
| 4,239,046 | 12/1980 | Ong | 128/640 |
| 4,243,044 | 1/1981 | Blancke | 128/696 |
| 4,257,424 | 3/1981 | Cartmell | 128/641 |
| 4,273,135 | 6/1981 | Larimore et al. | 128/640 |
| 4,300,575 | 11/1981 | Wilson | 128/798 |
| 4,331,153 | 5/1982 | Healy | 128/641 |
| 4,352,359 | 10/1982 | Larimore et al. | 128/640 |
| 4,353,372 | 10/1982 | Ayer | 128/640 |
| 4,365,634 | 12/1982 | Bare et al. | 128/640 |
| 4,370,984 | 2/1983 | Cartmell | 128/640 |
| 4,391,278 | 7/1983 | Cahalan et al. | 128/640 |
| 4,515,162 | 5/1985 | Yamamoto et al. | 128/640 |
| 4,554,924 | 11/1985 | Engel | 128/640 |

DRY ELECTRODE SYSTEM FOR DETECTION OF BIOPOTENTIALS

BACKGROUND OF THE INVENTION

1. Field of the Invention

The invention described herein pertains to the detection of potentials existing on the surface of the skin of the living body, which potentials are generated by various sources such as muscle or nervous system activity within the body.

2. Discussion of the Background

Present biopotential detection techniques typically involve the use of wet conductive pastes or gels in combination with a metallic contact surface to form an electrode capable of transforming ionic current flow in the body into electronic current flow in the measuring apparatus. There are several realizations of this basic type of electrode, and all of them suffer from the various disadvantages of wet systems, such as skin irritation, loss of electrical contact due to drying paste or lead wires falling off, poor shelf life, etc. Attempts have been made to eliminate the pastes and gels in two separate ways: the introduction of new electrode materials, and the incorporation of amplifier electronics into the electrode itself.

The materials introduced in the prior art as dry electrodes generally have not been accepted in the medical field due to poor performance. For example, most of the metals and conductive composite materials generate excessive low frequency electrical noise voltages when in contact with a saline solution such as the human sweat which invariably collects on the surface of the skin beneath the electrode, but there is little or no attention given to this problem in the prior art. Furthermore, many of these materials are too stiff to conform to irregularities in skin surface, thus resulting in an unstable dry skin contact subject to excessive movement artifact.

Another type of dry electrode material, conductive adhesive, has been disclosed, for example in U.S. Pat. No. 3,911,906, but is subject to limitations caused by the size of the electrode necessary for secure adhesion to the skin. In U.S. Pat. No. 3,911,906 the preferred size of the conductive adhesive is two inches in diameter, not to be greatly reduced. However, such a large area electrode detects signals from a large volume of tissue, which is not always desirable especially if the signal of interest is from a source distant from the electrode site. In this case, the increased level of electrical activity from the muscles directly below the electrode would result in excessive interference or artifact in the recording. Another drawback is the large water content of conductive adhesives such as described in U.S. Pat. No. 4,391,278, (35% to 75% by weight water) which limits the storage life of the material.

Another approach to realizing a dry electrode, placing an electronic amplifier on the electrode, is based on the idea that a high impedance amplifier is able to detect a signal from a high impedance source with a minimum of signal distortion, and then drive the signal through a long cable with a minimum of interference by virtue of the low output impedance of the amplifier. One problem is that many previously disclosed designs, including DC biased transistor amplifiers, differential amplifiers, and amplifiers with gains above unity are not compatible with commonly used monitoring equipment unless some adjustment or modification is made to the monitor. Even unity-gain, DC-biased transistor amplifiers that are capacitively coupled at the output cannot conveniently be used with different types of monitors without the risk of frequency distortion caused by impedance mismatching to the different monitor inputs, and without large transient DC offsets arising when switching leads. Another problem has been questionable reliability, as demonstrated by a group of devices utilizing a capacitively coupled input to an amplifier constructed on a metallic electrode coated with a dielectric. This type of electrode is prone to failure from dielectric breakdown due to scratches or high voltages, and exhibits undue sensitivity to external electrostatic fields.

A group of amplifiers using bipolar integrated circuit operational amplifiers with unity gain has been disclosed, but a means for adequately protecting the electronic circuitry from repeated exposure to high voltages, without compromising the essential electrical characterstics of the amplifier input, has not been demonstrated. Defibrillation voltages, static charge accumulation on the skin and clothes, and other medical equipment may cause potentials greater than 25,000 volts to contact the input to the electrode amplifier on a repeated basis, resulting in permanent failure of the device if not protected. The prior art shows the use of input resistors or unspecified current limiters for device and patient protection, but fails to show a means for compensating for the degradation of input impedance to the device as a result of parasitic capacitance coupling to ground through the resistor or current limiter. Furthermore, a single input resistor or current limiter may not provide adequate protection for some types of integrated circuit amplifiers such as CMOS devices which are sensitive to large input voltages rather than currents. Additionally, there previously has been no disclosure of a means for incorporating very small batteries into the amplifier or lead wire in order to continuously power the amplifier for a period of more than a year without prematurely exhausting the batteries. Due to excessive current demand by the amplifier, especially when the input is unconnected and the output has drifted to saturation as a result, it has previously been necessary to disconnect the batteries from the amplifier when not in use, either by physical removal or by means of a power switch, thus adding undesirable complexity to the operation of the electrode lead wire.

SUMMARY OF THE INVENTION

Accordingly, it is an object of the present invention to provide a new and improved dry electrode system for detecting potentials on the skin of a living body without the use of conductive pastes or gels under conditions ranging from dry to sweat-soaked skin.

A further object of this invention to provide a novel dry electrode system which is immune from destruction or instability caused by repeated exposure to high voltages over long time periods.

Yet another object of this invention is to provide a novel dry electrode system capable of providing a signal to conventional monitoring devices without the need for adjustment or modification to the monitor.

These and other objects are achieved according to the invention by providing novel dry electrode system for the detection of biopotentials existing on the skin of a living body, which biopotentials arise from generators within the body such as heart, muscle or nervous system activity, including a dry electrode pad formed of a resilient conductive pad having a dry conductive center and adhesive means for adhering the dry electrode pad to the skin and to a conductive contact. The conductive contact is coupled to the input of a lead amplifier having an output which is connected to a shield surrounding portions of the contact such that the shield is voltage driven by the output of the lead amplifier. The lead amplifier is attached to one end of a shielded multi-conductor lead cable which provides bipolar power supply voltages, common potential, and an output conductor to the lead amplifier. At the other end of the lead cable is provided a battery pack which in turn is connected to a lead wire connector suitable for interfacing with a monitor.

According to one embodiment of the invention, the conductive pad is mounted on an apertured insulative adhesive pad which has one adhesive surface adapted to adhere to the skin and an opposite adhesive surface adhering to the lead amplifier housing (or case). Alternatively, the conductive pad is sandwiched between opposed apertured adhesive pads.

In another embodiment, the opposed sides of the conductive pad are coated, except for central portions of the opposed sides, with respective adhesive coatings, the central portions being uncoated in order so as not to impede signal transmission.

The conductive pad is made of a resilient conductive material and makes electrical contact with the skin, yet prohibits direct physical contact by the conductive contact. This inhibits disease transmission, since the pad is disposable, and enables reuse of the lead wire contact and associated lead amplifier.

In a preferred embodiment, the lead amplifier is mounted in a small plastic case with the shielded electrical contact extending from the case. Additionally, the multi-conductor lead cable also is surrounded by a conductive shield which is either driven by a voltage follower amplifier connected to the output of the lead amplifier, or otherwise connected to common potential. Additionally, the lead amplifier has its input protected by a diode circuit which shunts bipolar currents to power supply common thereby to protect the high input impedance lead amplifier from high amplitude voltage sources. This diode circuit also provides a means for minimizing electrical power required by the lead amplifier, which enables the use of a miniature battery pack at the opposite end of the lead wire cable to power the lead amplifier continuously for long time periods.

The voltage-driven shield surrounds the input contact and an input resistor connecting the contact to the lead amplifier, and serves to maintain a high input impedance into the lead amplifier while shielding the input from external electric interference.

Dry ground contact for referencing the lead amplifier common potential to the body is implemented through an elastic conductive strap holding a disposable conductive pad in contact with the skin. An alternative dry ground electrode utilizes the dry electrode pad above described in combination with a passive lead wire connection.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1A:
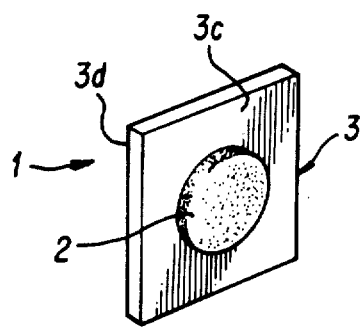
FIGS. 1a and 1b are perspective views of opposite sides of one embodiment of the adhesive pad with a conductive pad center of the dry electrode of the invention.
Figure 1B:
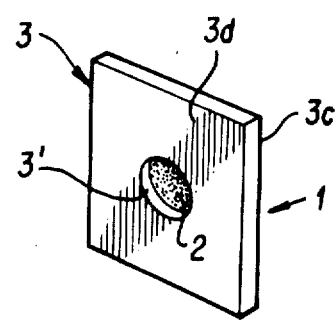

Referring now to the drawings, wherein like reference numerals designate identical or corresponding parts throughout the several views, and more particularly to FIGS. 1a-1d thereof, an embodiment of the dry electrode pad 1 of the present invention is shown. As shown in FIGS. 1a and 1b, the dry electrode pad 1 of the invention includes a resilient conductive pad 2 and an insulative adhesive pad 3. The conductive pad 2 is mounted over an aperture 3' formed in the center of the adhesive pad 3. The conductive pad 2 is a material with three essential traits: resiliency, electrical conductivity, and electrical stability. The material must be flexible in order to conform to a body surface contour yet possess a sufficient resiliency to maintain intimate contact with the skin despite dynamic variations in contour, for example due to breathing or similar bodily movement. Thus, the resiliency of the material forming the conductive pad 2 as measured by the Ball Rebound test (ASTM Designation D 3574 - 81) must exceed 5% and preferably be as high as 20%. It is furthermore essential that the electrical resistivity of the material not be greater than 200,000 ohm-cm and preferably that it be between 800 ohm-cm and 3200 ohm-cm, measured under the condition that the width of the dry material is compressed by 50%. Finally, the material must maintain an electrical stability in terms of self-generated AC noise voltages over a bandwidth of 0.15 HZ to 35 HZ, under conditions ranging from dry to saturation with a 0.9% saline solution. The maximum acceptable AC noise voltage is 150 microvolts peak value, although it is preferable to maintain noise voltages well below this value.

One material capable of meeting the above restrictions is low density, carbon loaded polyurethane foam, but it is understood that any material meeting the above specifications falls within the scope of the invention. If the material is a flexible cellular foam, an enhancement in electrode performance may be realized by coating or forming on the skin-side surface of the foam a thin, flexible, smooth coating or layer of curable conductive material meeting the conductivity and electrical stability restrictions outlined above, with the intent of maximizing the dry conductive contact area to the skin while maintaining the mechanical properties of the conductive pad as previously outlined. One example of such a surface is realized by mixing one and one half parts by volume graphite powder ($-300$ mesh, 99.5% pure) with five parts by volume distilled water and ten parts by volume liquid latex. A thin layer of this mixture is spread on a smooth glass surface and the conductive foam of 400 ohm-cm resistivity is held in contact with the mixture until it cures, resulting in a smooth conductive skin adhering to the surface of the foam. According to the invention, a conductive coating can also be formed on the opposite side of the conductive pad to achieve a further enhancement in electrode performance and to simply use in the field.

The dry electrode pad 1 as shown in FIGS. 1a-1d includes a compliant adhesive pad 3 made of a material such as cross-linked polyethylene foam. Adhesive pad 3 serves to hold the conductive pad 2 in contact with the skin while holding conductive pad 2 in contact with a conductive contact 6 discussed hereinafter. To this end, the skin-side 3c of the adhesive pad 3 is coated with a pressure sensitive hypoallergenic medical adhesive providing a tacky skin-engaging surface, while the lead-side 3d of the adhesive pad 3 is coated with a pressure sensitive removable adhesive of reduced tackiness to engage the lead. It is important that the lead-side adhesive is fully removable, i.e., it leaves no residue on the lead after removal in order to avoid contamination and disease transmission. One example of a suitable medical adhesive is Type MA-23 adhesive manufactured by Adhesives Research Inc., Glen Rock, Pa. An example of a suitable removable adhesive is Type AS-23 acrylic based adhesive, also manufactured by Adhesive Research, Inc.

Figure 1C:
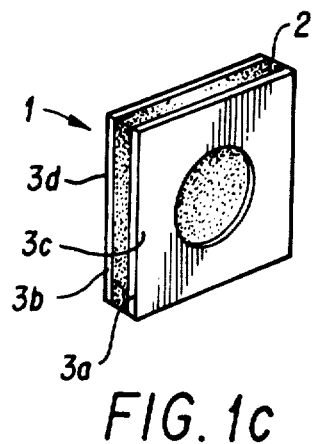
FIGS. 1c and 1d are perspective views of opposite sides of a second embodiment of the adhesive pad of the invention.
Figure 1D:
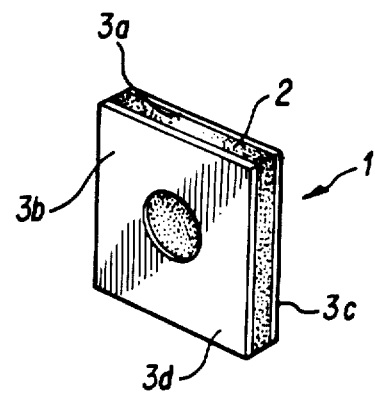

In the embodiment shown in FIGS. 1a and 1b, the dry electrode pad 1 includes a single adhesive pad 3 with a central aperture of slightly smaller diameter than the diameter of the conductive pad 2 while holding it firmly in place against the skin. Another embodiment of the adhesive pad, illustrated in FIGS. 1c and 1d, is a single conductive pad 2 with thin adhesive pads 3a and 3b mounted on both sides with central apertures to allow electrical contact to skin and a lead contact. As in FIG. 1a, the adhesives are of medical quality on the skin-side 3c and removable quality on the lead-side 3d. Other embodiments of the dry electrode pad 1 may have square or other shaped holes and other shapes of conductive pads and/or adhesive pads within the scope and spirit of the invention.

Figure 2:
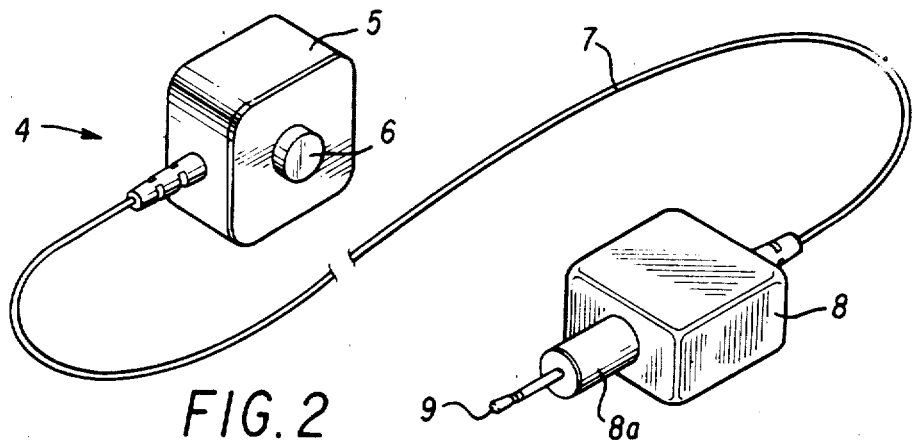
FIG. 2 is a perspective view of the inventive lead wire with lead amplifier housing and one embodiment of the battery housing and lead wire connector.

FIG. 2 shows an embodiment of the connective lead wire 4 which electrically engages the conductive pad 2 and is adhesively contacted by the adhesive pad 3. Lead wire 4 includes a lead amplifier housing 5 which has a lead amplifier input contact 6. The lead amplifier input contact 6 is a solid conductive material that meets the same electrical stability as the conductive pad under conditions ranging from dry to total immersion in a 0.9% saline solution. An appropriate material is press-molded titanium hydride but it is understood that other materials meeting the above requirements are acceptable as well. Alternatively, any solid conductive material may be used for input contact 6 if the dry electrode pad 1 in use is impervious to fluids. Part of input contact 6 may be a threaded section 31 (shown in FIG. 5) for mating with input connector 30. Alternatively, threaded section 31 may be deleted and input contact 6 affixed directly to input connector 30 by means of a conductive bonding agent such as silver cement. The amplifier housing 5 houses a lead amplifier circuit 10 discussed hereinafter and is made of an insulating material such as plastic or epoxy resin which is also impervious to fluids. A shielded cable 7 with four separate, insulated, internal conductors connects the output, ground, and power supply leads of the lead amplifier circuit 10 to a battery pack 8 and lead wire connector 9, which are shown in FIG. 2. In lieu of the batter pack 8 and connector 9, the lead amplifier circuit 10 may be connected directly to a monitor or other devices by means of a lead wire connector or permanently wired connection for providing supply current, ground and signal connections. The battery pack 8 supplies bipolar voltages of usually 1 to 3 volts and is encased in an insulating material such as plastic or epoxy. As shown in FIG. 2, the lead wire connector 9 is a miniature phone plug with the output signal and battery common (ground) connected to the plug. Other types of plugs may be used such as the standard pin plug, in which case there are two plugs at 9.

Figure 3:
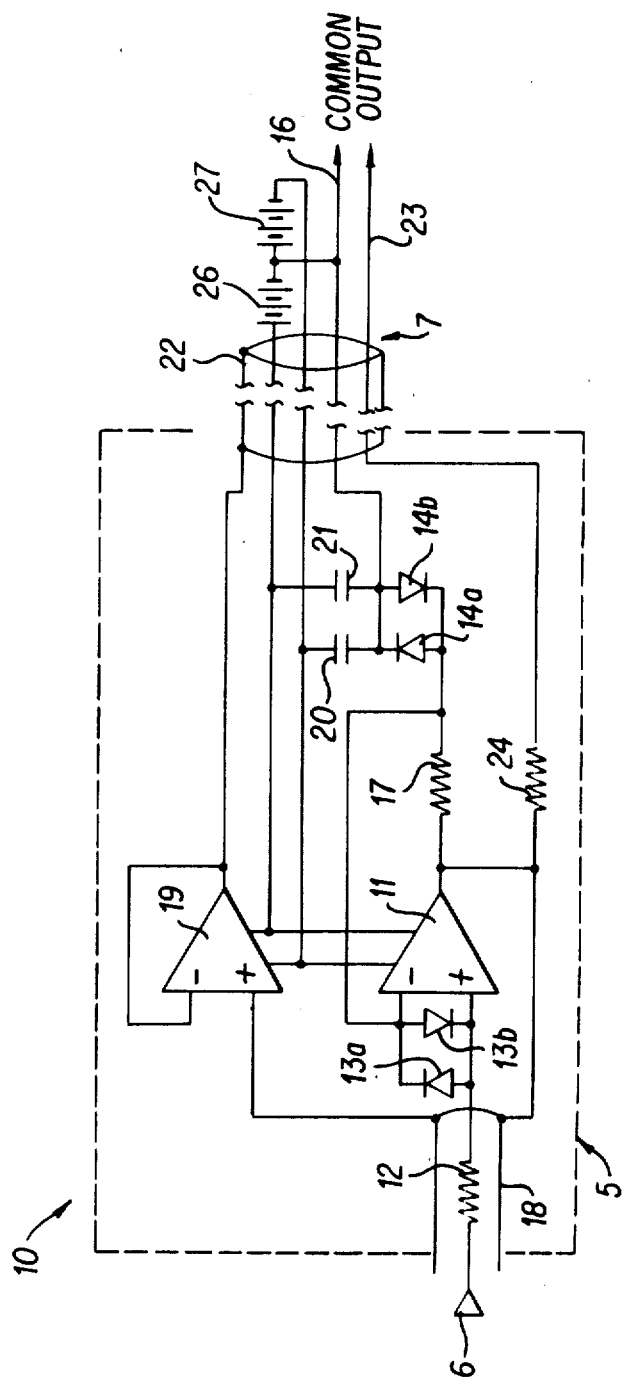
FIG. 3 is a circuit schematic of the lead wire amplifier according to the invention.

A circuit schematic of one embodiment of the lead amplifier circuit 10 is shown in FIG. 3. The insulating case 5 is represented by outer dotted-line and the conductive input contact 6 is shown at the edge of a voltage-driven shield 18 which is connected to the output of an operational amplifier 11 with noninverting unity gain. The input signal is conducted through resistor 12 which serves as a current limiter to prohibit fault currents above allowable limits from reaching the body. The inputs of amplifier 11 are protected from large amplitude voltages by signal diodes 13a, 13b, 14a and 14b, such as type 1N914, which shunt bipolar currents to battery common or ground 16 while preventing the voltage at the non-inverting input of amplifier 11 from rising to more than positive or negative 2 volts with respect to ground. Resistor 17, which may be 10,000 ohms, completes the feedback loop for amplifier 11 yet isolates its output from large currents that may flow in diodes 13a, 13b and 14a, 14b. A high input impedance into amplifier 11 of more than 10,000 megohms is maintained since diodes 13a and 13b have the same potential on both sides under normal operating conditions by virtue of the operational amplifier characterstics of amplifier 11. Furthermore, since the shield 18 is driven at the same potential as the input signal, any parasitic capacitance to ground through resistor 12 or connective input leads is minimized thus maintaining a measurably high input impedance and superior noise rejection characteristics of the lead wire amplifier circuit. Operational amplifier 19 is implemented in a unity gain, noninverting configuration in order to drive a lead wire shield 22 shielding the conductors of cable 7 at the same potential as that appearing on the output conductor 23, which results in improved shielding and lowered noise voltages generated by cable motion. It is understood that the outputs of amplifiers 11 and 19 may be nulled to zero offset by means of resistive connections (not shown) standard to the type of operational amplifiers used in the circuit, thereby maximizing the effects described above. Capacitors 20 and 21 are used in a common circuit technique to decouple the leads to the power supply batteries 26 and 27 from noise voltage sources, and resistor 24 isolates the output of 11 from the effects of capacitive loads.

Figure 4:
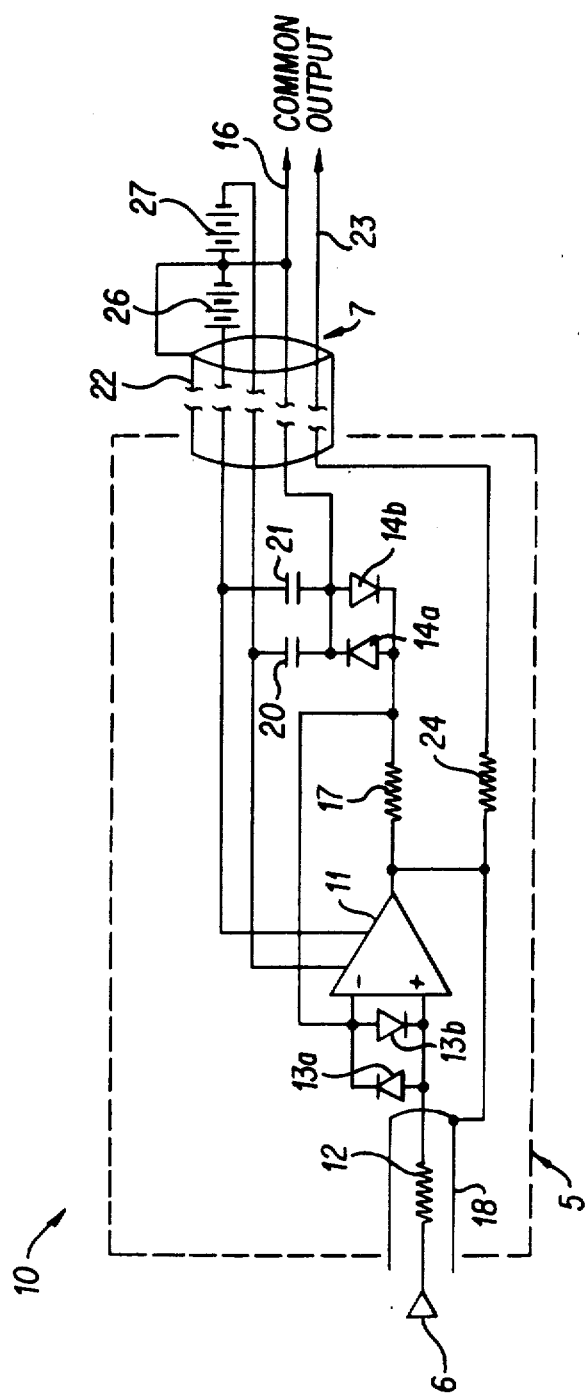
FIG. 4 is a circuit schematic of a minimum power lead amplifier according to the invention.

Another embodiment of the lead amplifier, shown in FIG. 4, dispenses with the shield driving amplifier 19 in order to minimize power supply requirements. The lead wire shield 22 in this example is connected to battery common 16 at the battery pack only, while the input contact shield is still voltage-driven by amplifier 11. Further reduction in power consumption can be realized by choosing low power integrated circuit amplifiers (such as CMOS types) exhibiting input offset voltages within a range of $-3$ mV to $+3$ mV and input bias currents of less than 50 pA.

An important feature in the circuit design of FIG. 4 resides in the input protection diodes 12 through 15 providing a pathway for sufficiently small bias currents from amplifier 11 when the input 6 is unconnected. Thus the output of amplifier 11 does not drift to one of the supply rails due to bias current charging the open input, and power consumption is limited to such a degree that it is no longer necessary to disconnect the batteries when the lead wire is not in use. Input impedance and open-input power consumption are directly related to the input offset voltage of operational amplifier 11; an input offset voltage range of $-3$ mV to $+3$ mV maintained without the aid of resistive nulling circuits has been shown to result in maximum input impedance while holding power consumption to a minimum. In low-power applications some CMOS operational amplifiers are not able to drive a signal into the capacitive load resulting from the grounded-shield cable configuration of FIG. 4. Therefore resistor 24 is important to the operation of the circuit in order to isolate the output of amplifier 11, and may be a 1% tolerance resistor of greater than 4000 ohms.

Alternative to the embodiments shown in FIGS. 3 and 4, the protective signal diode pairs 13a, 13b and 14a, 14b can be replaced with respective single Zener diode, i.e., each diode pair being replaced by a Zener diode. Any polarity orientation of the Zener diodes may be used. In order to obtain maximum protection for the operational amplifier 11 the Zener voltage should be less than 10 volts and preferably as small as possible. The use of the Zener diodes imposes a restraint on the value of input resistor 12; a resistance of not less than 1.5 megohms must be used in order to preserve the desired characteristics of the lead amplifier 11.

Since the Zener diodes serve the same function as the signal diode pairs in providing protection to the lead amplifier from large voltage transients, the advantage gained by their use is a reduction in the number of components of the lead amplifier. On the other hand, a disadvantage is apparent in the additional restraint imposed on the input resistor, whereas the signal diode pairs present no such restraint.

Figure 5A:
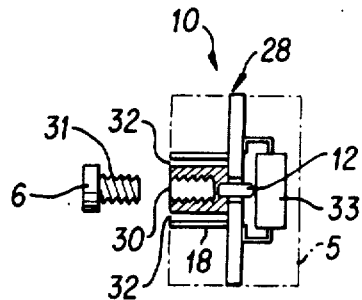
FIGS. 5a and 5b are schematic side and plan views, respectively, illustrating details of the physical geometry of an embodiment of the lead amplifier circuit board and driven shield, using a dual-in-line integrated circuit package.
Figure 5C:
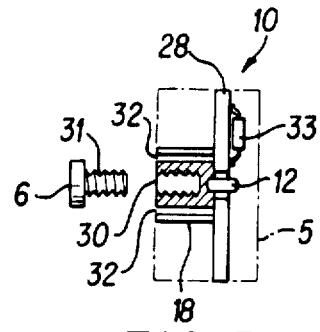
FIGS. 5c and 5d are respectively schematic side and plan views illustrating another embodiment of the lead amplifier circuit board and driven shield using a surface mount integrated circuit package and components.
Figure 5B:
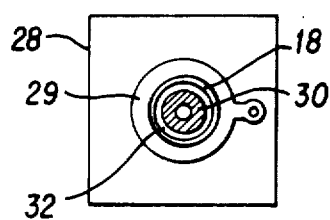

Details of the shielding and physical construction of an embodiment of the lead amplifier are shown in FIGS. 5a and 5b. A circuit board 28 with a circular guard ring 29 surrounding input resistor 12 is depicted in FIGS. 5a and 5b. Resistor 12 fits into a hole in circuit board 28, with one end soldered directly to the amplifier input trace on the component side of circuit board 28 and the opposite end soldered to input connector 30 which is threaded to accept the threaded section 31 of input contact 6. Alternatively, input connector 30 may be a solid conductive material with a protruding surface incorporating input contact 6 into a single piece. A metal tube 18 soldered to guard ring 29 and isolated from input connector 30 by insulative material 32 provides shielding for the extent of input connector 30. Guard ring 29 and hence shield 18 are connected to the output of amplifier 11 thus providing a voltage-driven input shield. The dual-in-line integrated circuit package 33 of amplifier 11 is positioned directly above resistor 12 in order to minimize the length of the input trace, and is soldered to traces on only the component side of circuit board 28 without inserting the metal leads through holes in 28 so as to avoid accidental contact to the shielding.

Figure 5D:
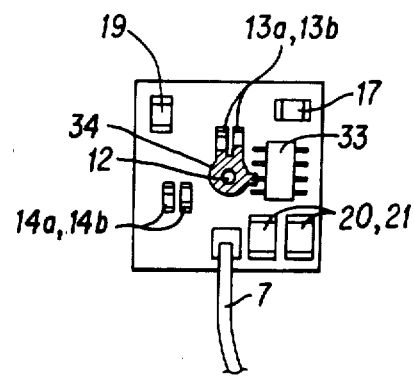

Alternatively, as shown in FIGS. 5c and 5d, a surface mount integrated circuit package 33 containing amplifier 11 is positioned directly next to resistor 12 and diodes 13a and 13b in order to minimize the length of input trace 34. The input contact shield and circuit side guard ring remain the same as in FIG. 5b. By using surface mount components for most or all of the circuit elements of the lead wire amplifier as illustrated in FIGS. 5c and 5b, it is possible to greatly reduce the physical size of the lead wire amplifier while realizing an economical manufacturing process. Furthermore, the shielding configuration of the invention as described above achieves superior shielding while eliminating the need for the bulky and potentially dangerous conductive shielding amplifier cases described in the prior art.

A ground or reference contact to the body is necessary to maintain a quiet stable signal and to provide a path for DC leakage currents. The ground or reference contact is a direct connection to the skin and is passive, i.e., it is made without the use of lead wire amplifiers. For patient safety the ground contact is usually connected to an isolated circuit common in the monitor amplifier instead of actual earth ground. For each dry electrode lead in contact with the body, lead common 16 is connected to both the body ground electrode and the isolated ground input of the monitor.

Figure 6A:
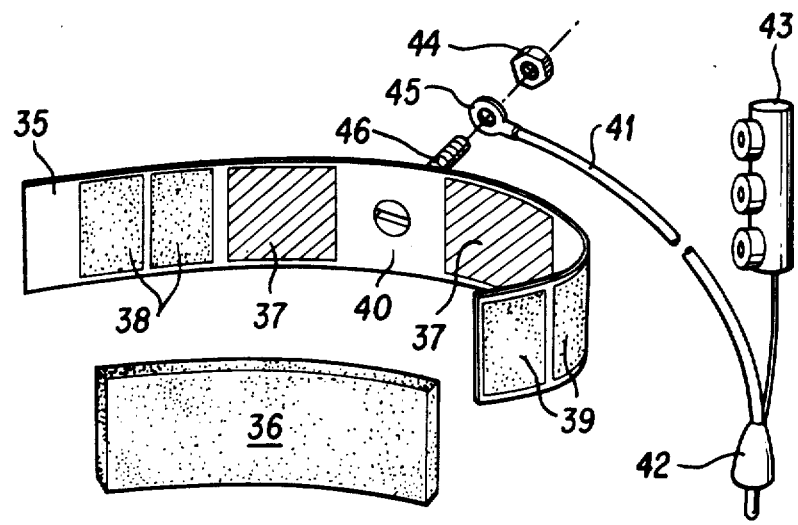
FIGS. 6a and 6b are perspective views of respective embodiments of the dry ground electrode, an elastic conductive strap and conductive foam pad, and an adhesive pad and passive lead wire contact according to the invention.
Figure 6B:
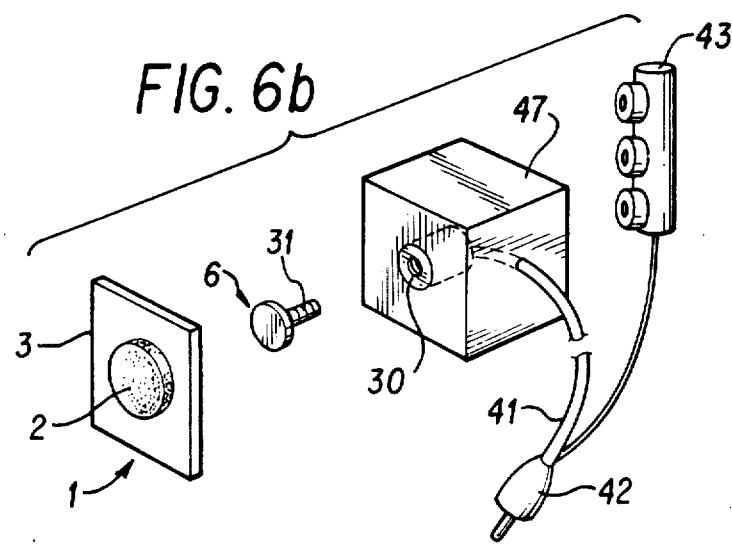

Two approaches as illustrated in FIGS. 6a and 6b are used according to the present invention to realize a stable dry ground electrode connection. In FIG. 6a, an adjustable elastic strap 35 is used to hold in contact with the skin of the arm or leg a strip of conductive pad 36 meeting the same specifications as described above for conductive electrode pads 2. Pad 36 makes electrical connection to the ground lead wire 41 via the conductive inside surface 37 of the elastic strap 35; the adjustable size of strap 35 is further extended through a connective system such as velcro(tm) hooks 39 and pads 38 in order to hold a snug but comfortable fit on any size arm or leg. The conductive surface 37 may be an elastic material interwoven with conductive metallic strands similar to devices used for the control of static charge accumulation on the body.

However, surface 37 must remain isolated by pad 36 from direct contact to the skin in order to avoid noise voltages generated by sweat contamination. Lead wire 41 is held in contact to conductive material 37 by a conductive plate 40, screw 46 and nut 44, and connective eyelet 45. In the embodiment shown in FIG. 6a, a pin plug 42 and pin jacks 43 provide a connective means to the ground electrode input of a monitor and the lead wire common connectors from the common conductors 16 of lead wire cable 7, although it is understood that other types of connectors may be used.

An alternative ground electrode connection utilizing the dry electrode pad 1 is illustrated in FIG. 6b and employs the passive elements shown in FIGS. 3 and 4, i.e., amplifiers and associated electrical components are deleted. The ground lead wire 41 connects to the body through the electrode pad 1 by means of an input contact 6 composed of conductive material as described above, with screw threads 31 mating to the threaded input connector 30. Alternatively, input connector 30 is a single conductive component incorporating contact 6, or else contact 6 without screw threads 31 may be attached to input connector 30 by a bonding agent such as silver cement. In both cases, lead wire 41 is connected directly to input connector 30, and the connective plug 42 and jacks 43 are the same as in the embodiment of FIG. 6a. In both embodiments of FIGS. 6a and 6b, ground lead wire 41 may be a shielded cable with the shield connected to ground at the monitor input.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A dry electrode system for the detection of biopotentials existing on the surface of the skin of a living body, comprising:
   a dry electrode pad comprising a resilient conductive pad having opposed sides, one of which is adapted to contact the skin of said living body, and adhesive means, having first and second adhesive surfaces, said first adhesive surface adapted to adhere said dry electrode pad to said skin;
   an amplifying circuit adapted to be connected to the other side of said conductive pad for amplifying a biopotential transmitted via said conductive pad to said amplifying circuit, comprising,
   an insulating housing adhering to said second adhesive surface of the dry electrode pad,
   a conductive input contact means mounted on said housing for engaging the dry electrode pad,
   a lead amplifier having an input coupled to said input contact means and an output, and
   a voltage driven first shield connected to said output of said lead amplifier and surrounding portions of said input contact means not in engagement with said pad.

2. A dry electrode system according to claim 1, wherein said conductive pad comprises:
   a resilient material having not less than 5% rebound value, dry resistivity not greater than 200,000 ohm-cm, and an AC noise base line not greater than 150 μV peak (0.15 to 35 Hz) under conditions of dry to saturation within a 0.9% saline solution.

3. A dry electrode system according to claim 2, wherein said conductive pad comprises:
   carbon loaded polyurethane foam.

4. The dry electrode system as defined in claim 3, wherein said conductive input contact means comprises a material that maintains an AC noise voltage baseline of not more than 150 μV peak (0.15 to 35 Hz) under conditions ranging from dry to saturation with a 0.9% saline solution.

5. A dry electrode system according to claim 4, wherein said conductive input contact means comprises a titanium hydride contact.

6. A dry electrode system according to claim 3, wherein said conductive input contact means comprises a titanium hydride contact.

7. The dry electrode system as defined in claim 2, wherein said conductive input contact means comprises a material that maintains an AC noise voltage baseline of not more than 150 μV peak (0.15 to 35 Hz) under conditions ranging from dry to saturation with a 0.9% saline solution.

8. The dry electrode system as defined in claim 1, wherein said conductive input contact means comprises a material that maintains an AC noise voltage baseline of not more than 150 μV peak (0.15 to 35 Hz) under conditions ranging from dry to saturation with a 0.9% saline solution.

9. A dry electrode system according to claim 1, wherein said conductive input contact means comprises a titanium hydride contact.

10. A dry electrode system according to claims 1, 2, 3, 8, 7, 4, 9, 6, or 5, wherein:
    said first adhesive surface comprises a hypoallergenic adhesive material, and
    said second adhesive surface comprises an adhesive material which leaves no adhesive residue on said housing after removal from said housing.

11. A dry electrode system according to claims 2, 3, 8, 7, 4, 9, 6 or 5, comprising:
    a flexible conductive film provided on at least one side of said conductive pad, said conductive film maintaining an AC noise voltage (0.15 to 35 Hz) of not more than 150 μV peak under conditions ranging from dry to saturation with a 0.9% saline solution.

12. A dry electrode system according to claim 11, wherein said conductive film is provided on both opposed sides of said conductive pad.

13. A dry electrode system according to claim 11, wherein said conductive film comprising:
    a cured mixture of one and one half parts by volume graphite powder, five parts by volume distilled water and ten parts by volume of liquid latex.

14. A dry electrode system according to claim 11, wherein said adhesive means comprises an adhesive coating formed on a portion of said flexible conductive film provided on said at least one surface of said conductive pad.

15. A dry electrode system according to claim 11, wherein:
    said first adhesive surface comprises a hypoallergenic adhesive material, and
    said second adhesive surface comprises an adhesive material which leaves no adhesive residue on said housing after removal from said housing.

16. A dry electrode system according to claim 1, wherein said adhesive means comprises:
    an adhesive pad on which said conductive pad is mounted, said adhesive pad having said first and second adhesive surfaces and including an aperture, said conductive pad mounted over said aperture on said first surface.

17. A dry electrode system according to claim 1, wherein said adhesive means comprises:
    opposed adhesive pads sandwiching said resilient conductive pad therebetween, said adhesive pads each having an aperture and said resilient conductive pad mounted therebetween, said adhesive pads having respective exterior adhesive surfaces serving as said first and second surfaces.

18. A dry electrode system according to claim 1, comprising:

a flexible conductive film provided on one side of said conductive pad, said conductive film maintaining an AC noise voltage (0.15 to 35 Hz) of not more than 150 µV peak under conditions ranging from dry to saturation with a 0.9% saline solution.

19. A dry electrode system according to claim 18, wherein said conductive film is provided on both opposed sides of said conductive pad.

20. A dry electrode system according to claim 1, wherein said adhesive means comprises:
   first and second adhesive coatings formed on portions of respective opposed sides of said conductive pad and serving as said first and second adhesive surfaces, respectively.

21. A dry electrode system according to claim 1, wherein said amplifying circuit comprises:
   said lead amplifier comprising an operational amplifier having inverting and non-inverting inputs,
   first and second diodes connected in parallel inverse polarity across the inputs of said operational amplifier,
   third and fourth diodes connected in parallel inverse polarity from the inverting input of said amplifier to a circuit common potential,
   an output resistor connected from the inverting input to the output of said operational amplifier,
   an input resistor connected between the non-inverting input of said operational amplifier and said conductive input contact means, said input resistor at least partially contained within said voltage-driven first shield,
   a lead wire cable having plural conductors connected to said amplifier and supplying power and common potential to said lead amplifier and taking out an output from said lead amplifier, and
   a decoupling resistor connected from the output of said operational amplifier to an output conductor of the lead wire cable.

22. A dry electrode system according to claim 21, further comprising:
   a circuit board having opposed sides, wherein on one of said sides of said circuit board said operational amplifier, said first through fourth diodes, and said output and decoupling resistors are mounted, said circuit board having an aperture through which said input resistor extends from the one side to the other side on which said conductive input contact means is mounted.

23. A dry electrode system according to claim 22, wherein said lead wire cable comprises:
   a flexible insulated multi-conductor cable including a pair of insulated conductors to carry bipolar supply currents to said lead amplifier, an insulated conductor to carry said circuit common potential to and from said lead amplifer, said output conductor comprising an insulated conductor to carry an output signal from said lead amplifier, and a second shield shielding said insulated conductors.

24. A dry electrode system according to claim 23, wherein said amplifying circuit further comprises:
   a voltage follower operational amplifier having a non-inverting input connected to the first shield, an inverting input connected to an output of said voltage follower operational amplifier and to said second shield.

25. A dry electrode system according to claim 23, wherein said second shield is connected to said insulated conductor carrying said circuit common potential.

26. A dry electrode system according to claim 23, comprising:
   means for providing said circuit common potential, including,
   an elastic ground strap having conductive portions and adapted to be mounted on a portion of the body,
   a second resilient conductive pad contacting said conductive portions of said strap, and
   a ground lead wire electrically conductively coupled between said second conductive pad and said insulated conductor carrying said circuit common potential.

27. A dry electrode system according to claim 23, comprising:
   means for providing said circuit common potential, including,
   a second dry electrode pad also comprising a resilient conductive pad having opposed sides one of which is adapted to engage the skin of the living body, and adhesive means having first and second adhesive surfaces, said first adhesive surface adapted to adhere to said second conductive pad to the skin of said living body,
   a second electrical contact means mounted on a second housing for adhering to said second surface of said adhesive means of said second dry electrode pad, said secohd contact means adapted to electrically contact said second conductive pad, and
   passive lead wire means for electrically conductively coupling said second electrical contact means to said conductor carrying said circuit common potential.

28. A dry electrode system according to claim 27, comprising:
   a conductive shield at least partially surrounding said second electrical contact means.

29. A dry electrode pad for enabling electrical and mechanical connection between the skin of a living body and an amplifying circuit electrically coupled to a monitor, comprising:
   a resilient conductive pad having first and second opposed sides and a flexible conductive film applied to at least one of said sides, said flexible conductive film adapted to contact the skin of said living body; and
   adhesive means having opposed first and second adhesive surfaces provided on selected portions of said conductive pad, said conductive pad adhering to said adhesive means, said first adhesive surface adapted to adhere to the skin such that said flexible conductive film of said conductive pad is in electrical contact with the skin, said second adhesive surface adapted to adhesively engage said amplifying circuit with the other side of said conductive pad electrically in connection with said amplifying circuit.

30. A dry electrode pad according to claim 29, comprising:
   a conductive film applied to the other side of said conductive pad and adapted to make electrical connection to said amplifying circuit.

31. A dry electrode pad according to claim 29, wherein said conductive pad comprises:
   a resilient foam material having not less than 5% rebound value, dry resistivity not greater than 200,000 ohm-cm, and an AC noise base line not greater than 150 µV peak (0.15 to 35 Hz) under conditions of dry to saturation within a 0.9% saline solution.

32. A dry electrode pad according to claim 31, wherein said conductive pad comprises:
   carbon loaded polyurethane foam.

33. A dry electrode according to claim 32, wherein said flexible conductive film maintains an AC noise voltage (0.15 to 35 Hz) of not more than 150 μV peak under conditions ranging from dry to saturation with a 0.9% saline solution.

34. A dry electrode according to claim 33, wherein said flexible conductive film comprises:
   a cured mixture of one and one half parts by volume graphite powder, five parts by volume distilled water and ten parts by volume of liquid latex.

35. A dry electrode pad according to claims 29, 30, 31, 32, 33, or 34, wherein said adhesive means comprises:
   an adhesive pad a first surface of which has said conductive pad mounted thereon and the second surface of which is adapted to adhesively engage said amplifying circuit.

36. A dry electrode pad according to claims 29, 30, 31, 32, 33, or 34, wherein said adhesive means comprises:
   a pair of apertured adhesive pads sandwiching said conductive pad.

37. A dry electrode pad according to claims 29, 30, 31 or 32, wherein said adhesive means comprises:
   adhesive coatings applied to portions of the opposed sides of said conductive pad.

38. A dry electrode pad according to claims 33 or 34, wherein said adhesive means comprises:
   an adhesive coating provided on portions of said conductive film.

39. A dry electrode system according to claim 35, wherein:
   said first adhesive surface comprises a hypoallergenic adhesive material, and
   said second adhesive surface comprises an adhesive material which leaves no adhesive residue on said housing after removal from said housing.

40. A dry electrode system according to claim 36, wherein:
   said first adhesive surface comprises a hypoallergenic adhesive material, and
   said second adhesive surface comprises an adhesive material which leaves no adhesive residue on said housing after removal from said housing.

41. A dry electrode system according to claim 37, wherein:
   said first adhesive surface comprises a hypoallergenic adhesive material, and
   said second adhesive surface comprises an adhesive material which leaves no adhesive residue on said housing after removal from said housing.

42. A dry electrode system according to claim 38, wherein:
   said first adhesive surface comprises a hypoallergenic adhesive material, and
   said second adhesive surface comprises an adhesive material which leaves no adhesive residue on said housing after removal from said housing.

43. A dry electrode system for the detection of biopotentials existing on the surface of the skin of a living body, comprising:
   a dry electrode pad comprising a resilient conductive pad and having opposed sides, one of which is adapted to contact the skin of said living body, and adhesive means, having first and second adhesive surfaces, said first adhesive surface adapted to adhere said resilient conductive pad to said skin, said resilient conductive pad comprising a flexible conductive film provided on at least one of the opposed sides of said resilient conductive pad, said conductive film maintaining an AC noise voltage (0.15 to 35 Hz) of not more than 150 μV peak under conditions ranging from dry to saturation with a 0.9% saline solution; and
   an amplifying circuit means adapted to adhere to said second adhesive surface and to be connected to the other side of said conductive pad for amplifying a biopotential transmitted via said dry electrode pad to said amplifying circuit means.

44. A dry electrode system according to claim 43, wherein said amplifying circuit means comprises:
   an insulating housing adhering to said second adhesive surface of the dry electrode pad;
   conductive input contact means mounted on said housing for engaging the dry electrode pad;
   a lead amplifier having inverting and noninverting inputs, one of which is coupled to said input contact means, and an output;
   first and second diodes connected in parallel inverse polarity across the inputs of said lead amplifier; and
   third and fourth diodes connected in parallel inverse polarity from the inverting input of said lead amplifier to a circuit common potential.

45. A dry electrode system according to claim 44, comprising:
   a voltage driven first shield connected to said output of said lead amplifier and surrounding portions of said input contact means not in engagement with said pad.

46. The dry electrode system as defined in claims 44 or 45, wherein said conductive input contact means comprises a material that maintains an AC noise voltage baseline of not more than 150 μV peak (0.15 to 35 Hz) under conditions ranging from dry to saturation with a 0.9% saline solution.

47. A dry electrode system according to claim 46, wherein said conductive input contact means comprises a titanium hydride contact.

48. A dry electrode system according to claims 43, 44, or 45, wherein:
   said first adhesive surface comprises a hypoallergenic adhesive material, and
   said second adhesive surface comprises an adhesive material which leaves no adhesive residue on said housing after removal from said housing.

49. A dry electrode system according to claim 45, wherein said amplifying circut means comprises:
   said lead amplifier comprising an operational amplifier,
   an output resistor connected from the inverting input to the output of said operational amplifier,
   an input resistor connected between the noninverting input of said operational amplifter and said conductive input contact means, said input resistor at least partially contained within said voltage-driven first shield,
   a lead wire cable having plural conductors connected to said lead amplifier and supplying power and common potential to said lead amplifier and taking out an output from said lead amplifier, and a decoupling resistor connected from the output of said operational amplifier to an output conductor of the lead wire cable.

50. A dry electrode system according to claim 49, wherein said lead wire cable comprises:
a flexible insulated multi-conductor cable including a pair of insulated conductors to carry bipolar supply currents to said lead amplifier, an insulating conductor to carry said circuit common potential to and from said lead amplifier, said output conductor comprising an insulated conductor to carry an output signal from said lead amplifier, and a second shield shielding said insulated conductors.

51. A dry electrode system according to claim 51, wherein said amplifying circuit means further comprises:
a voltage follower operational amplifier having a non-inverting input connected to the first shield, an inverting input connecting to an output of said voltage follower operational amplifier and to said second shield.

52. A dry electrode system according to claim 51, wherein said second shield is connected to said insulated conductor carrying said circuit common potential.

53. A dry electrode system according to claim 43, wherein said conductive pad comprises a resilient material having not less than 5% rebound value, and wherein said conductive pad has a dry resistivity not greater than 200,000 ohm-cm, and an AC noise base line not greater than 150 μV peak (0.15 to 35 Hz) under conditions of dry to saturation within a 0.9% saline solution.

54. A dry electrode system according to claim 43, wherein said conductive pad comprises:
carbon loaded polyurethane foam.

55. A dry electrode system according to claim 43, wherein said adhesive means comprises:
at least one adhesive pad on which said conductive pad is mounted.

56. A dry electrode system according to claim 43, wherein said adhesive means comprises:
opposed adhesive pads sandwiching said resilient conductive pad therebetween.

57. A dry electrode system according to claim 56, wherein said adhesive pads each having an aperture and said resilient conductive pad is mounted therebetween.

58. A dry electrode system according to claim 43 wherein said conductive film is provided on both opposed sides of said conductive pad.

59. A dry electrode system according to claim 58, wherein said conductive film comprising:
a cured mixture of one and one half parts by volume graphite powder, five parts by volume distilled water and ten parts by volume of liquid latex.

60. A dry electrode system according to claim 43 wherein said adhesive means comprises an adhesive coating formed on a portion of said flexible conductive film provided on said at least one side of said conductive pad.

61. A dry electrode system according to claim, 43, wherein said adhesive means comprises:
first and second adhesive coatings formed on portions of respective opposed surfaces of said conductive pad and serving as said first and second adhesive surfaces, respectively.

* * * * *

UNITED STATES PATENT AND TRADEMARK OFFICE
CERTIFICATE OF CORRECTION

PATENT NO. : 4,669,479
DATED : June 2, 1987
INVENTOR(S) : W.J. ROSS DUNSEATH, JR.

It is certified that error appears in the above-identified patent and that said Letters Patent is hereby corrected as shown below:

Column 1, line 31, change "excessive" to --excessively--;

line 64, change "DC biased" to --DC-biased--.

Column 2, line 54, after "invention" insert --is--;

line 63, after "providing" insert --a--.

Column 5, line 19, change "simply" to --simplify--;

line 38, change "Adhesive" to --Adhesives--.

Column 6, line 13, change "batter" to --battery--;

line 39, change "non-inverting" to --noninverting--;

line 49, change "characterstics" to --characteristics";

line 56, change "unity gain" to --unity-gain--.

UNITED STATES PATENT AND TRADEMARK OFFICE
CERTIFICATE OF CORRECTION

PATENT NO. : 4,669,479
DATED : June 2, 1987
INVENTOR(S) : W.J. ROSS DUNSEATH, JR.

It is certified that error appears in the above-identified patent and that said Letters Patent is hereby corrected as shown below:

Column 8, line 9, delete "board" (second occurrence).

Column 9, line 24, change "livino" to --living--;

line 43, between "voltage" and "driven" insert a hyphen;

line 59, change "baseline" to --base line--.

Column 10, lines 3 and 9, change "baseline" to --base line--;

line 35, change "comprising" to --comprises--;

line 43, change "surface" to --side--;

Column 11, lines 18, 27, 28 and 62, change "non-inverting" to --noninverting--.

UNITED STATES PATENT AND TRADEMARK OFFICE
CERTIFICATE OF CORRECTION

PATENT NO. : 4,669,479

DATED : June 2, 1987

INVENTOR(S) : W.J. ROSS DUNSEATH, JR.

It is certified that error appears in the above-identified patent and that said Letters Patent is hereby corrected as shown below:

Column 12, line 28, change "secohd" to --second--;

line 34, change "." to --,--.

Column 13, line 20, change "the" to --a--.

Column 14, line 34, between "voltage" and "driven" insert a hyphen;

line 41, change "baseline" to --base line--;

line 55, change "circut" to --circuit--;

line 61, change "amplifter" to --amplifier--.

Column 15, line 15, change "51" (second occurrence) to --50--;

line 19, change "non-inverting" to --noninverting--;

UNITED STATES PATENT AND TRADEMARK OFFICE
CERTIFICATE OF CORRECTION

PATENT NO. : 4,669,479
DATED : June 2, 1987
INVENTOR(S) : W.J. ROSS DUNSEATH, JR.

Page 4 of 4

It is certified that error appears in the above-identified patent and that said Letters Patent is hereby corrected as shown below:

Column 15, line 20, change "connecting" to --connected--;

line 24, change "51" to --50--.

Column 16, line 13, change "having" to --have--;

line 19, change "comprising" to --comprises--.

Signed and Sealed this

Fifth Day of July, 1988

*Attest:*

DONALD J. QUIGG

*Attesting Officer*  *Commissioner of Patents and Trademarks*